United States Patent
Pereira et al.

(10) Patent No.: US 12,234,319 B2
(45) Date of Patent: *Feb. 25, 2025

(54) SEALANT COMPOSITION

(71) Applicant: TISSIUM SA, Paris (FR)

(72) Inventors: Maria Pereira, Lisbon (PT); Elsa Brillaud, Villejuif (FR)

(73) Assignee: TISSIUM SA, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/404,513

(22) Filed: Jan. 4, 2024

(65) Prior Publication Data

US 2024/0141099 A1    May 2, 2024

Related U.S. Application Data

(63) Continuation of application No. 15/737,103, filed as application No. PCT/EP2016/064015 on Jun. 17, 2016, now Pat. No. 11,898,005.

(60) Provisional application No. 62/181,270, filed on Jun. 18, 2015.

(30) Foreign Application Priority Data

Jun. 18, 2015 (EP) .................................... 15172795

(51) Int. Cl.
| | |
|---|---|
| *C08G 63/47* | (2006.01) |
| *A61L 24/00* | (2006.01) |
| *A61L 24/04* | (2006.01) |
| *A61L 26/00* | (2006.01) |
| *C08G 63/50* | (2006.01) |
| *C08G 63/91* | (2006.01) |
| *C08J 3/24* | (2006.01) |
| *C09J 167/06* | (2006.01) |
| *C09J 167/07* | (2006.01) |

(52) U.S. Cl.
CPC .......... *C08G 63/47* (2013.01); *A61L 24/0042* (2013.01); *A61L 24/046* (2013.01); *A61L 26/0019* (2013.01); *A61L 26/009* (2013.01); *C08G 63/50* (2013.01); *C08G 63/918* (2013.01); *C08J 3/24* (2013.01); *C08J 3/246* (2013.01); *C09J 167/06* (2013.01); *C09J 167/07* (2013.01); *C08J 2367/06* (2013.01); *C08J 2367/07* (2013.01)

(58) Field of Classification Search
CPC ........ C08G 63/20; C08G 63/47; C08G 63/50; C08G 63/918; C09J 167/06; C09J 167/07; B33Y 10/00; B29C 64/00–40
See application file for complete search history.

(56) References Cited

U.S. PATENT DOCUMENTS

| | | |
|---|---|---|
| 4,035,439 A | 7/1977 | Stevenson |
| 2003/0078339 A1 | 4/2003 | Kiser et al. |
| 2009/0047256 A1 | 2/2009 | Bettinger et al. |
| 2011/0008277 A1 | 1/2011 | Bruggeman et al. |
| 2013/0231412 A1 | 9/2013 | Langer et al. |
| 2014/0147472 A1 | 5/2014 | Elimelech et al. |
| 2015/0072293 A1* | 3/2015 | DeSimone ............ B33Y 30/00 355/18 |

FOREIGN PATENT DOCUMENTS

| | | |
|---|---|---|
| CN | 1993388 A | 7/2007 |
| CN | 101087860 A | 12/2007 |
| CN | 101111272 A | 1/2008 |
| CN | 101801322 A | 8/2010 |
| CN | 102176890 A | 9/2011 |
| CN | 102596275 A | 7/2012 |
| CN | 103083718 A | 5/2013 |
| CN | 103459529 A | 12/2013 |
| CN | 104144999 A | 11/2014 |
| GB | 1125258 A | 8/1968 |
| JP | A-S49-24245 | 3/1974 |
| JP | A-H2-238013 | 9/1990 |
| JP | 2009-523864 | 6/2009 |
| JP | 2016-526078 | 9/2016 |
| WO | WO 2000/051662 | 9/2000 |
| WO | WO 2012/042522 | 5/2012 |
| WO | WO 2014/190302 A1 | 11/2014 |

OTHER PUBLICATIONS

Christiaan L. E. Nijst et al., "Synthesis and Characterization of Photocurable Elastomers from Poly (glycerol-co-sebacate)", Biomacromolecules 2007, vol. 8, No. 10, pp. 3067-3073.
Extended European Search Report regarding EP 21 177 746, Jul. 12, 2021, European Patent Office.
International Search Report, issued by the European Patent Office, mailed Aug. 30, 2016, 2 pp.
Naolou et al., "Fatty Acid Modified Poly(glycerol adipate)—Polymeric Analogues of Glycerides," in Tailored Polymer Architectures for Pharmaceutical and Biomedical Applications, ACS Symposium Series, 39-52 (2013).
Scifinder properties of CAS 25248-42-4 (2019).

* cited by examiner

*Primary Examiner* — Kregg T Brooks
(74) *Attorney, Agent, or Firm* — Finnegan, Henderson, Farabow, Garrett & Dunner, LLP

(57) ABSTRACT

A composition with improved adhesive and sealant properties comprises a) a pre-polymer comprising a polymeric unit of the general formula $(-A-B-)_n$, wherein A represents a substituted or un-substituted ester, B represents a substituted or un-substituted acid ester comprising at least two acid ester functionalities, and n represents an integer greater than 1; wherein the content of grafted anhydride in the composition is less than 0.05 mol/mol of polyacid.

10 Claims, 5 Drawing Sheets

SEALANT COMPOSITION

This application is a continuation of application Ser. No. 15/737,103, filed Dec. 15, 2017, which is a national stage application under 35 U.S.C. § 371 of International Patent Application No. PCT/EP2016/064015, filed Jun. 17, 2016, which claims the benefit of EP 1517 2795.5, filed Jun. 18, 2015, which claims the benefit of U.S. Provisional Application No. 62/181,270, filed Jun. 18, 2015, all of which are incorporated herein by reference.

FIELD OF INVENTION

The present invention relates to a composition, a method of manufacturing the composition, a method of curing the composition, a cured composition obtainable therefrom, uses of the composition and methods of using the composition.

BACKGROUND OF THE INVENTION

Open heart surgery typically relies on a suture-based closure or attachment of cardiovascular structures. However, this can be technically challenging due to the fragility of young infant tissue and diseased or damaged adult tissue, leading to longer operative times, increased risk of complications of bleeding or dehiscence, and therefore worse outcomes. Furthermore, cardiopulmonary bypass (CPB) is required for open heart surgery, and this has significant adverse effects, including an inflammatory response and potential neurological complications.

While catheter-based interventions for closure of cardiac defects such as atrial and ventricular septal defects (ASDs and VSDs) have recently emerged in an effort to reduce the invasiveness of the procedures, major challenges remain with securing devices inside the beating heart. Specifically, fixation of devices for catheter-based closure of cardiac septal defects currently relies on mechanical means of gripping tissue. This can cause injury to critical structures, such as heart valves or specialized conduction tissue. Furthermore, if inadequate tissue rims exist around defects, the prosthesis may dislodge, damaging the neighboring structures and also leaving residual defects, limiting device application. Therefore, such methods can only be applied in select patients, depending on the anatomic location and the geometric shape of the defect.

Soft and compliant tissue sealants that cure rapidly, have significant sealant properties, are biocompatible and work in the presence of blood offer a potential solution. They could be used to attach tissue surfaces together or prosthetic devices to tissue without the need for mechanical entrapment or fixation, thereby avoiding tissue compression and erosion, and may also be utilized in minimally invasive surgical procedures. Such materials could find a broad range of applications not only in minimally invasive cardiac repair, but also in the repair of soft tissues potentially with minimal scarring and damage. For example, in vascular surgery, suture-based anastomosis does not always result in an instantaneous hemostatic seal, and can create irregularities in the endothelium that predispose to thrombosis. Furthermore, the presence of permanent sutures can cause a foreign body reaction with further inflammation and scarring at the repair site, which may increase the risk of late vessel occlusion. Tissue sealants could accomplish such repairs with an instantaneous seal and with minimal scarring or tissue damage.

An ideal tissue sealant, especially for cardiovascular and/or gastrointestinal applications, should have most of the following properties: (1) optimal viscosity or liquid-like properties prior to curing to enable easy application to a desired area while being retained at the application site, (2) minimum washout by body fluids and activation only when desired to facilitate its delivery and repositioning of implanted devices during minimally invasive procedures, (3) significant adhesive strength, especially in the presence of blood and/or other body fluids, (4) ability to resist the mechanical loads from adhesion to highly mobile tissue, for example contractions of the heart, or pulsations in large vessels, (5) ability to form a hemostatic and/or hermetic seal, (6) minimal inflammatory response, and (7) biodegradability, which is determinant for the healing process, especially important for pediatric applications since the long-term consequences of foreign materials in the growing body are uncertain.

Unfortunately, current clinically-available sealants, such as medical grade cyanoacrylate (CA) or fibrin sealant, are easily washed out or cured under dynamic wet conditions, toxic and therefore cannot be used internally, and/or exhibit weak sealant and/or adhesive properties such that they cannot withstand the forces inside the cardiac chambers and major blood vessels. Also, many of these sealants exhibit activation properties that make fine adjustments or repositioning of the devices very difficult. Moreover, many sealants under development achieve tissue seals only through chemical reaction with functional groups at the tissue surface, and thus become ineffective in the presence of blood.

Alternatives to cyanoacrylate have been explored. U.S. Pat. No. 8,143,042 B2 describes biodegradable elastomers prepared by crosslinking a prepolymer containing crosslinkable functional groups, such as acrylate groups. It also discloses that it is desirable to increase the number of free hydroxyl groups on the polymer in order to increase the stickiness of the polymer. Increasing the number of hydroxyl groups in the backbone also leads to enhanced hydrophobicity solubility in physiologic solutions. This suggests that the primary mechanism of adhesion of the polymer is chemical interactions between functional groups, for example free hydroxyl groups on the polymer and the tissue to which it is applied. However, this type of chemical interaction becomes ineffective in the presence of body fluids, especially blood, as shown in Artzi et al., Adv. Mater. 21, 3399-3403 (2009).

Similarly, Mandavi, et al., 2008, *PNAS*, 2307-2312, describes nanopatterned elastomeric polymer and proposes applying a thin layer of oxidized dextran with aldehyde functionalities (DXTA) to increase adhesion strength of the adhesive by promoting covalent cross-linking between terminal aldehyde group in DXTA with amine groups in proteins of tissue.

This adhesion mechanism based essentially on covalent bonding between the radicals generated during the curing process and functional groups of the tissue has several limitations. The use of adhesives with reactive chemistry requires tissue surfaces to be dried prior to application of the pre-polymer, which makes it very challenging to use in cardiac application, such as during emergency procedures. Additionally, reactive chemistry can denature proteins or tissue and promote undesirable immune reaction such as local inflammation which can lead to adhesive rejection. Moreover, reactive chemistry that only bonds to the surface of tissue would likely have lower adhesion as the interface would be more distinct, and thus there would be a mismatch in mechanical properties at the interface between the glue and tissue.

Elastomeric crosslinked polyesters are disclosed in US 20130231412 A1. Biodegradable polymers are disclosed in U.S. Pat. No. 7,722,894 B2. Adhesive articles are disclosed in WO2009067482 A1 and WO2014190302 A1. Blood resistant surgical glue is described in "A Blood-Resistant Surgical Glue for Minimally Invasive Repair of Vessels and Heart Defects" Sci Transl Med 8 Jan. 2014: Vol. 6, Issue 218, p. 218ra6, Nora Lang, Maria Pereira et al. and WO2014190302 A1. However, there still exists a need for an improved and commercially viable tissue sealant/adhesive that can be readily applied to the desired site, remains in place at the desired site prior to curing and is not washed away by bodily fluids, is biocompatible (non-toxic), and exhibits strong sealant/adhesive forces, such as those encountered inside the cardiac chambers and major blood vessels even in the presence of bodily fluids, such as blood.

SUMMARY OF THE INVENTION

The present invention provides a composition comprising:
- a pre-polymer comprising a polymeric unit of the general formula $(-A-B-)_n$, wherein A represents a substituted or un-substituted ester, B represents a substituted or un-substituted acid ester comprising at least two acid ester functionalities, and n represents an integer greater than 1;
- wherein the content of grafted anhydride in the composition is less than 0.05 mol/mol of polyacid.

The present invention also provides a method for manufacturing the composition according to the present invention.

The present invention further provides a method of curing the composition according to the present invention, comprising curing the composition with a stimulus, for example light in the presence of a photo-initiator.

The present invention also provides a cured composition obtainable by the curing method according to the present invention. According to preferred embodiment, said cured composition is a sealant, i.e. can provide a seal, preventing the leakage of fluids or gas The present invention further provides methods of use and use of the composition according to the present invention for gluing or sealing tissue or for adhering tissue to the surface of a medical device.

The present invention also provides a method for sealing tissue, the method comprising applying the composition according to the present invention to the surface of the tissue and curing the composition.

The present invention further provides a method for adhering tissue to the surface of a medical device, the method comprising applying the composition according to the present invention to the surface of the tissue and/or medical device and curing the composition. In preferred embodiments, a medical device can be adhered to another medical device, or parts of medical devices can be adhered together in the assembly of a medical device.

DETAILED DESCRIPTION OF THE INVENTION

Pre-Polymer

Figure 1:
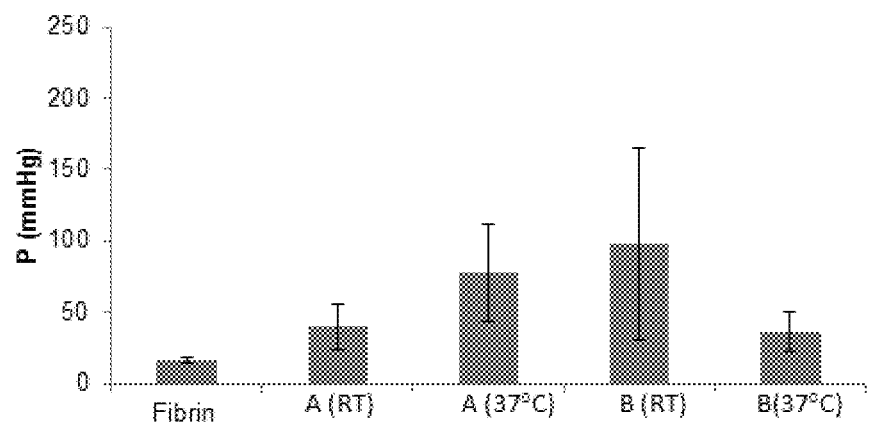
FIGS. 1 to 3 and 5 are graphs showing burst performance of compositions according to the present invention.

The pre-polymer according to the present invention comprises a polymeric unit of the general formula $(-A-B-)_n$, wherein A represents a substituted or un-substituted ester, B represents a substituted or un-substituted acid or acid ester comprising at least two acid or acid ester functionalities; and n represents an integer greater than 1.

Component A may be derived from a polyol, such as a diol, triol, tetraol or greater. Suitable polyols include diols, such as alkane diols; triols, such as glycerol, trimethylolpropane, triethanolamine; tetraols, such as erythritol, pentaerythritol; and higher polyols, such as sorbitol. Unsaturated diols, such as tetradeca-2,12-diene-1,14-diol, or other diols including macromonomer diols such as, for example polyethylene oxide, and N-methyldiethanoamine (MDEA) can also be used. Preferably, the polyol is substituted or unsubstituted glycerol.

Component B may be derived from a polyacid, such as a diacid or higher order acid. A wide variety of diacid, or higher order acids, can be used. Exemplary acids include, but are not limited to, glutaric acid (5 carbons), adipic acid (6 carbons), pimelic acid (7 carbons), sebacic acid (8 carbons), and azelaic acid (nine carbons). Exemplary long chain diacids include diacids having more than 10, more than 15, more than 20, and more than 25 carbon atoms. Non-aliphatic diacids can also be used. For example, versions of the above diacids having one or more double bonds can be used to produce polyol-diacid co-polymers. Preferably the diacid is substituted or unsubstituted sebacic acid.

Polyol-based polymers described in US Patent Application Publication 2011-0008277, U.S. Pat. Nos. 7,722,894 and 8,143,042, the contents of which are hereby incorporated by reference, can also be used as a pre-polymer to form elastomeric polymeric materials Several substituents, such as amines, aldehydes, hydrazides, acrylates and aromatic groups, can be incorporated into the carbon chain. Exemplary aromatic diacids include terephthalic acid and carboxyphenoxy-propane. The diacids can also include sub stituents as well. For example, reactive groups like amine and hydroxyl can be used to increase the number of sites available for cross-linking. Amino acids and other biomolecules can be used to modify the biological properties. Aromatic groups, aliphatic groups, and halogen atoms can be used to modify the inter-chain interactions within the polymer.

The pre-polymer may further comprise a polyamide or polyurethane backbone. For example, polyamine (comprising two or more amino groups) may be used to react with polyacid together with polyol or after reacting with polyol.

Exemplary poly(ester amide) includes those described in Cheng, et al., Adv. Mater. 2011, 23, 1195-11100, the contents of which are herein incorporated by reference. In other examples, polyisocianates (comprising two or more isocyanate groups) may be used to react with polyacid together with polyol or after reacting with polyol. Exemplary polyester urethanes include those described in US2013231412.

The weight average molecular weight of the pre-polymer, measured by Gel Permeation Chromatography equipped with a refractive index, may be from about 1,000 Daltons to about 1,000,000 Daltons, from about 1,000 Daltons to about 1,000,000 Daltons, preferably from about 2,000 Daltons to about 500,000 Daltons, more preferably from about 2,000 Daltons to about 250,000 Daltons, most preferably from about 2,000 Daltons to about 100,000 Daltons. The weight average molecular weight may be less than about 100,000 Dalton, less than about 75,000 Daltons, less than about 50,000 Daltons, less than about 40,000 Daltons, less than about 30,000 Daltons, or less than about 20,000 Daltons. The weight average molecular weight may be from about 1000 Daltons to about 10,000 Daltons, from about 2000 Daltons to about 10,000 Daltons, from about 3000 Daltons to about 10,000 Daltons from about 5,000 Daltons to about 10,000 Daltons. Preferably, it is about 3000 Daltons.

The term "about" as used herein means within 10%, preferably within 8%, and more preferably within 5% of a given value or range. According to specific embodiment, "about X" means X.

The pre-polymer may have a polydispersity, measured by Gel Permeation Chromatography equipped with a refractive index, below 20.0, more preferably below 10.0, more preferably below 5.0, and even more preferably below 2.5. Preferably, it is about 2.5.

The pre-polymer may have a melt viscosity at 80° C. between 100 and 2000 cP, more preferably between 200 and 1000 cP and even more preferably between 300 and 500 cP.

The pre-polymer may have an acid number between 1 and 200 mg KOH/g of polymer, more preferably between 10 and 100 mg KOH/g of polymer, and even more preferably between 50 and 100 mg KOH/g of polymer. Preferably, it is about 80 mg KOH/g of polymer The molar ratios of the polyol to the polyacid in the pre-polymer may be 1:1, 1:2, 1:3, 1:4, 1:5, 1:6, 1:7, 1:8, 1:9 and 1:10. 10:1, 9:1, 8:1, 7:1, 6:1, 5:1, 4:1, 3:1, 2:1, 1:1. The molar ratios of polyol to the polyacid may also be 2:3, 3:2, 3:4, or 4:3. The polymer may also be the result of a mixture of two or more different ratios. Preferably, it is about 1:1.

Activated Pre-Polymer

The pre-polymer of the present invention is preferably activated. It can be activated by introducing functional groups that can react or be reacted to form crosslinks. The pre-polymer is activated by reacting one or more functional groups on the pre-polymer backbone with one or more functional groups that can react or be reacted to form crosslinks resulting in cured polymer.

Suitable functional groups to be activated on the pre-polymer backbone include hydroxy groups, carboxylic acid groups, amines, and combinations thereof, preferably hydroxy and/or carboxylic acid. The free hydroxyl or carboxylic acid groups on the pre-polymer can be activated by functionalizing the hydroxy groups with a moiety which can form a crosslink between polymer chains. The groups that are activated can be free hydroxyl or carboxylic acid groups on A and/or B moieties in the pre-polymer.

The free hydroxy or carboxylic groups can be functionalized with a variety of functional groups, for example vinyl groups. Vinyl groups can be introduced by a variety of techniques known in the art, such as by vinylation or acrylation. According to the present invention, vinyl groups contain the following structure —$CR_1$=$CR_2R_3$ wherein $R_1$, $R_2$, $R_3$ are independently from one another, selected in the group consisting of H, alkyl such as methyl, ethyl, aryl such as phenyl, substituted alkyl, substituted aryl, carboxylic acid, ester, amide, amine, urethane, ether, and carbonyl.

Preferably, the functional group is or contains an acrylate group. According to the present invention, acrylate groups are moieties containing substituted or unsubstituted acryloyl group. The acrylate may contain the following group: —C(=O)—$CR_1$=$CR_2R_3$, wherein $R_1$, $R_2$, $R_3$ are independently from one another, selected in the group consisting of H, alkyl such as methyl or ethyl, aryl such as phenyl, substituted alkyl, substituted aryl, carboxylic acid, ester, amide, amine, urethane, ether, and carbonyl.

Preferably, $R_1$, $R_2$ and $R_3$ are H; or $R_1$ is $CH_3$, $R_2$ and $R_3$ are H; or $R_1$ and $R_2$ are H and $R_3$ is $CH_3$; or $R_1$ and $R_2$ are H and $R_3$ is phenyl.

Vinyl groups can also be incorporated in the backbone of the pre-polymer using free carboxyl groups on the pre-polymer. For example, hydroxyethyl methacrylate can be incorporated through the COOH groups of the pre-polymer using carbonyl diimidazole activation chemistry.

The degree of activation can vary and can be from 0.2 to 0.9 mol/mol of polyacid or polyol, preferably from 0.3 to 0.8 mol/mol of polyacid or polyol and most preferably from 0.4 to 0.6 mol/mol of polyacid or polyol, such as 0.5 mol/mol of polyacid or polyol for achieving optimal bust performance properties at room temperature or elevated temperature up to 40° C., preferably 37° C. It is most preferred when the degree of activation is as described above and the reactive functional group is acrylate i.e. degree of acrylation as above.

The activated pre-polymer preferably has the general formula (I):

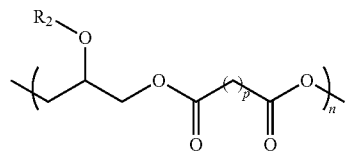

wherein n and p each independently represent an integer equal or greater than 1, and wherein $R_2$ in each individual unit represents hydrogen or a polymer chain or —C(=O)—$CR_3$=$CR_4R_5$, wherein $R_3$, $R_4$, $R_5$ are independently from one another, selected in the group consisting of H, alkyl such as methyl or ethyl, aryl such as phenyl, substituted alkyl, substituted aryl, carboxylic acid, ester, amide, amine, urethane, ether, and carbonyl.

Preferably, $R_3$, $R_4$ and $R_5$ are H; or $R_3$ is $CH_3$, $R_4$ and $R_5$ are H; or $R_3$ and $R_4$ are H and $R_5$ is $CH_3$; or $R_3$ and $R_4$ are H and $R_5$ is phenyl.

Preferably, p is an integer from 1-20, more preferably from 2-10, even more preferably from 4-10. It is most preferred when p=8.

The preferred pre-polymer has the following structure:

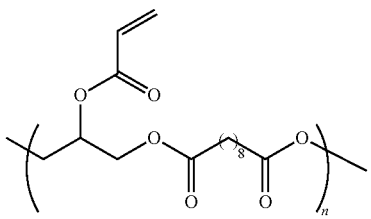

wherein n represents an integer equal or greater than 1

In addition to acrylates or other vinyl groups, other agents can be used to activate the pre-polymer. Examples of such agents include, but are not limited to, glycidyl, epichlorohydrin, triphenylphosphine, diethyl azodicarboxylate (DEAD), diazirine, divinyladipate, and divinylsebacate with the use of enzymes as catalysts, phosgene-type reagents, di-acid chlorides, bis-anhydrides, bis-halides, metal surfaces, and combinations thereof. Agents may further include isocyanate, aldehyde, epoxy, vinyl ether, thiol, DOPA residues or N-Hydroxysuccinimide functional groups.

The activated pre-polymer can be further reacted with one or more additional materials to modify the crosslinks between the polymer chains. For example, prior to or during curing/crosslinking, one or more hydrogel or other oligomeric or monomeric or polymeric precursors (e.g., precursors that may be modified to contain acrylate groups) such as poly(ethylene glycol), dextran, chitosan, hyaluronic acid, alginate, other acrylate based precursors including, for example, acrylic acid, butyl acrylate, 2-ethylhexyl acrylate, methyl acrylate, ethyl acrylate, acrylonitrile, n-butanol, methyl methacrylate, acrylic anhydride, methacrylic anhydride and TMPTA, trimethylol propane trimethacrylate, pentaerythritol trimethacrylate, pentaerythritol tetramethacrylate, ethylene glycol dimethacrylate. dipentaerythritol penta acrylate, Bis-GMA (Bis phenol A glycidal methacrylate) and TEGDMA (tri-ethylene, glycol dimethacrylate), sucrose acrylate; other thiol based precursors (monomeric or polymeric); other epoxy based precursors; and combinations thereof, can be reacted with the acrylated pre-polymer (e.g., PGSA).

The activated pre-polymer may be manufactured in the presence and/or mixed with a coloring agent. Preferred examples of coloring agents are the ones recommended by the FDA for use in medical devices, pharmaceutical products or cosmetics. See http://www.fda.gov/ForIndustry/ColorAdditives/ColorAdditiveInventories/. More preferably, this agent is FD&C 1.

Anhydrides

The inventors of the present invention have realized that anhydride compounds may be generated from the activation of the pre-polymer, for example through the reaction of acryloyl chloride (AcCl) and free carboxylic acids. An example of such an anhydride has general formula (II):

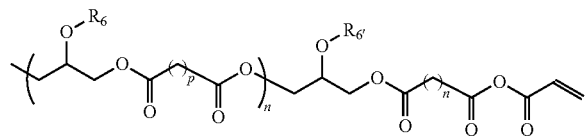

wherein p and n each individually represent an integer equal or greater than 1; wherein $R_6$ and $R_{6'}$ in each individual unit are independent and can be a polymer chain or $R_6$ and $R_{6'}$ in each individual unit are independent and can be —C(=O)—$CR_3$=$CR_4R_5$, wherein $R_3$, $R_4$, $R_5$ are independently from one another, selected from the group consisting of H, alkyl such as methyl or ethyl, aryl such as phenyl, substituted alkyl, substituted aryl, carboxylic acid, ester, amide, amine, urethane, ether, and carbonyl; or $R_6$ and $R_{6'}$ in each individual unit are independent and can be alkyl, aryl, heterocycles, cycloalkyl, aromatic heterocycles, multicycloalkyl, ester, ether, halide, carboxylic acid, amino, alkylamino, dialkylamino, trialkylamino, amido, carbamoyl, thioether, thiol, alkoxy, or ureido groups.

p can be an integer from 1-20, from 2-10, or even from 4-10, such as when p=8.

The anhydride can have the following structure:

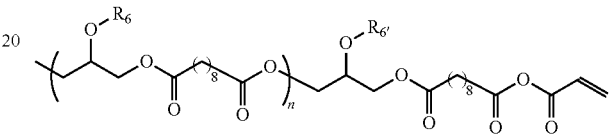

wherein $R_6$ or $R_{6'}$ independently represent a polymer chain or

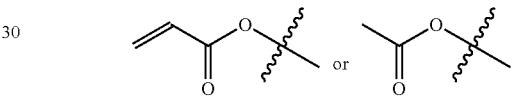

During activation of the pre-polymer, both asymmetric and symmetric anhydride can be generated.

An assymetric anhydride (also referred as mixed anhydride) is a carboxylic acid anhydride that has the following general structural formula:

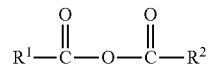

wherein R1 and R2 are different, and R1 and R2 are selected in the group of hydrogen atoms, alkyl groups, aryl groups.

A symmetric anhydride is a carboxylic acid anhydride that has the following general structural formula:

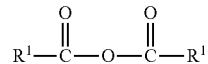

wherein R1 is selected in the group of hydrogen atoms, alkyl groups, aryl groups.

The inventors of the present invention have now shown that this presence of anhydrides is correlated with instability of the pre-polymer, leading to increasing level of impurities (e.g. low molecular weight acrylates) over time and to composition being very difficult to apply. It was thus necessary to obtain stable composition comprising the pre-polymer which might be used as sealant and/or adhesive with limited change in the level of impurities over time, limited evolution in molecular weight, and therefore limited change in viscosity.

According to the present invention the molar ratio of the total content of grafted anhydride in the composition is less than 0.05 mol/mol of polyacid as measured by nuclear magnetic resonance (NMR). Preferably there is no grafted anhydride present in the composition. More preferably there is no anhydride, grafted or non-grafted, present in the composition.

The content of grafted anhydride in the composition can be controlled during synthesis by ethanol capping or using any other nucleophilic substitution reaction. These chemical reactions are well known in the art. Suitable reagents for this reaction include alcohols, amines or sulfhydryl compounds. The addition of ethanol is preferably at a temperature in the range of 30 to 50° C., preferably 35 to 45° C., for example 40° C. The duration of the ethanol capping step is conducted preferably during 10 and 40 hours, more preferably during 24 hours. The volumetric ratio of polymer solution (~10% w/v) to ethanol is in the range of 20:1, more preferably in the range of 10:1 and even more preferably in the rage of 5:1.

Upon the capping steps, the structure of the free carboxylic acid ends in the activated pre-polymer chains becomes:

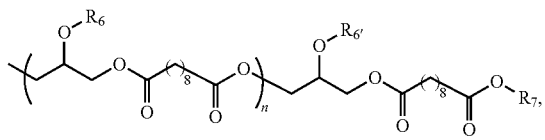

wherein p and n each individually represent an integer equal or greater than 1; wherein $R_6$ and $R_{6'}$ in each individual unit are independent and can be a polymer chain or $R_6$ and $R_{6'}$ in each individual unit are independent and can be —C(=O)—$CR_3$=$CR_4R_5$, wherein $R_3$, $R_4$, $R_5$ are independently from one another, selected from the group consisting of H, alkyl such as methyl or ethyl, aryl such as phenyl, substituted alkyl, substituted aryl, carboxylic acid, ester, amide, amine, urethane, ether, and carbonyl; or $R_6$ and $R_{6'}$ in each individual unit are independent and can be —H, alkyl, aryl, heterocycles, cycloalkyl, aromatic heterocycles, multicycloalkyl, ester, ether, halide, carboxylic acid, amino, alkylamino, dialkylamino, trialkylamino, amido, carbamoyl, thioether, thiol, alkoxy, or ureido groups; wherein $R_7$ is selected from the group consisting of —H, alkyl such as methyl or ethyl, aryl such as phenyl, substituted alkyl, substituted aryl, amine, urethane, thiol or thioester.

In the case of capping with ethanol $R_7$ is —$CH_2CH_3$

Unreacted nucleophilic groups may be partially or totally blocked or protected after pre-polymer activation. Examples of blocking or protection reactions are well known in the art. Hydroxyl protecting or blocking groups include acyl; cyclic or acyclic, branched or unbranched, substituted or unsubstituted alkyl; cyclic or acyclic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; or cyclic or acylic, branched or unbranched, substituted or unsubstituted heteroalkynyl; substituted or unsubstituted aryl; or substituted or unsubstituted heteroaryl.

Curing

The composition according to the present invention can be a surgical composition and can be used as tissue sealants and/or adhesives. The composition has flow characteristics such that they can be applied to the desired area through a syringe or catheter but is sufficiently viscous to remain in place at the site of application without being washed away by bodily fluids, such as water and/or blood.

Preferably, the viscosity of the composition is 500 cP to 100000 cP, more preferably 1000 to 50000 cP, even more preferably 2000 to 40000 cP and most preferably 2500 to 25000 cP. Viscosity analysis is performed using a Brookfield DV-II+Pro viscosimeter with a 2.2 mL chamber and SC4-14 spindle, the speed during the analysis is varied from 5 to 80 rpm. The above mentioned viscosity is present in the relevant temperature range for medical application i.e. room temperature up to 40° C., preferably 37° C.

The composition is also sufficiently hydrophobic to resist washout by bodily fluids, such as blood. This facilitates delivery to the desired site as well as repositioning of devices implanted using the composition of the invention during minimally invasive surgery. Hydrophobicity is dependent on the chemical composition of the pre-polymer, including the hydrophobic nature of the polymer backbone (for example longer alkyl chain are more hydrophobic than shorter chains) and the degree of activation. The pre-polymer of the present invention may already contain crosslinks before curing, but typically is not fully crosslinked as it is soluble in organic solvents such as dichloromethane or ethyl acetate. The composition of the invention may be incubated in bodily fluids, such as blood, prior to administration and curing, without a substantial decrease in sealant strength when cured.

The composition of the invention is stable in bodily fluids, such as blood. More particularly, the composition of the invention does not spontaneously crosslink in bodily fluids absent the presence of an intentionally applied stimulus such as light, for example UV light, heat, or chemical initiator to initiate crosslinking.

The composition can be cured using a free radical initiated reaction, such as, for example, by photo-initiated polymerization, thermally-initiated polymerization, and redox initiated polymerization.

Preferably, the composition is irradiated with light, for example ultraviolet (UV) light in the presence of a photoinitiator to facilitate the reaction. Examples of suitable photoinitiators include, but are not limited to: 2-dimethoxy-2-phenyl-acetophenone, 2-hydroxy-1-[4-(hydroxyethoxy) phenyl]-2-methyl-1-propanone (Irgacure 2959), 1-hydroxycyclohexyl-1-phenyl ketone (Irgacure 184), 2-hydroxy-2-methyl-1-phenyl-1-propanone (Darocur 1173), 2-benzyl-2-(dimehylamino)-1-[4-morpholinyl) phenyl]-1-butanone (Irgacure 369), methylbenzoylformate (Darocur MBF), oxy-phenyl-acetic acid-2-[2-oxo-2-phenyl-acetoxyethoxy]-ethyl ester (Irgacure 754), 2-methyl-1-[4-(methylthio)phenyl]-2-(4-morpholinyl)-1-propanone (Irgacure 907), diphenyl(2,4,6-trimethylbenzoyl)-phosphine oxide (Darocur TPO), phosphine oxide, phenyl bis(2,4,6-trimethyl benzoyl) (Irgacure 819), and combinations thereof.

Preferably, the composition is irradiated with visible light (typically blue light or green light) in the presence of a photoinitiator to facilitate the reaction. Examples of photoinitiators for visible light include, but are not limited to, diphenyl(2,4,6-trimethylbenzoyl)-phosphine oxide, eosin Y disodium salt, N-Vinyl-2-Pyrrolidone (NVP) and triethanolamine, and camphorquinone.

In applications of the composition involving in vivo photopolymerization and other medical applications, the use of cytocompatible photoinitiators is preferred and may be required by regulatory agencies. Photoinitiator Irgacure 2959 may be used which causes minimal cytotoxicity (cell death) over a broad range of mammalian cell types and species, however it is possible to reduce this risk by using non toxic amounts.

In order for the photopolymerization to occur, the composition (and the substrate to which is it applied, if applicable) is preferably sufficiently transparent to the light, even if it is colored.

In applications when the composition is cured in vivo, the temperature at which curing occurs is preferably controlled as not damage the tissue on which the composition has been applied. This control can be managed by reducing the curing light exposure time (e.g. less than 60 sec, preferably less than 30 sec). Preferably, the composition is not heated above 45° C. during irradiation, more preferably not above 37° C., and even more preferably not above 25° C.

In addition to photochemical crosslinking, the composition can be cured thermally, by Mitsunobu-type reaction, by redox-pair initiated polymerization for example benzoyl peroxide, N,N,-dimethyl-p-toluidine, ammonium persulfate, or tetramethylenediamine (TEMED), and by a Michael-type addition reaction using a bifunctional sulfhydryl compound.

Upon polymerization, the pre-polymer forms a cross-linked network with improved sealant properties and exhibits significant sealant strength even in the presence of blood and other bodily fluids. The sealant of the Invention obtained after curing is preferably sufficiently elastic to resist movement of the underlying tissue, for example contractions of the heart and blood vessels. The sealant can provide a seal, preventing the leakage of fluids or gas. The sealant is preferably biodegradable and biocompatible, causing minimal inflammatory response. The sealant is preferably elastomeric.

Biodegradability can be evaluated in vitro, such as in phosphate buffered saline (PBS) or in acidic or alkaline conditions. Biodegradability can also be evaluated in vivo, such as in an animal, for example mice, rats, dogs, pigs or humans. The rate of degradation can be evaluated by measuring the loss of mass and/or thickness of the polymer over time in vitro or in vivo.

The cured composition can exhibit a burst pressure of greater than 80 mmHg, preferably in the range of 100 mmHg to 200 mmHg or greater, for example 400 mmHg or 500 mmHg. Burst pressure or strength refers to the pressure value obtained to burst an explanted porcine carotid arterial vessel which has an incision coated with the composition.

The cured composition, alone or coated on a patch or tissue also preferably exhibits a 90° pull off adhesive strength of at least 0.3 N/cm$^2$, more preferably at least 0.5 N/cm$^2$ and even more preferably at least 2 N/cm$^2$, for example 1.5N/cm$^2$ to 2N/cm$^2$, or greater. Pull off adhesive strength refers to the adhesion value obtained by attaching an adhesive article or sample to wet tissue, such as epicardial surface of cardiac tissue, blood vessels, or the serosol side of porcine intestine tissue, immobilized on a flat substrate, such as a metallic stub. The 90° pull off adhesion test determines the greatest perpendicular force (in tension) that a surface area can bear before adhesive detachment.

According to preferred embodiment, the composition of the invention is cured in light and in presence of a photo initiator and the cured composition exhibits a 90° pull off adhesive strength of at least 0.5 N/cm$^2$, preferably at least 1 N/cm$^2$ and even more preferably at least 2 N/cm$^2$, for example 1.5N/cm$^2$ to 2N/cm$^2$, but preferably greater than 5 N/cm$^2$, for example up to 6 N/cm$^2$ or 7 N/cm$^2$ or greater.

The composition of the present invention when cured in light and in the presence of a photo-initiator preferably has one or more of the following properties:
i) 90° pull off strength greater than 0.3 N/cm$^2$, preferably 0.5 N/cm$^2$ or greater; and
ii) burst performance of greater than 80 mmHg, preferably 100 to 200 mmHg or greater.

The composition of the present invention is used as sealant, i.e.is able after curing of preventing leaking (e.g. fluid, gas) by forming a barrier or filling a void volume.

According to a preferred embodiment, the composition of the invention is also used as adhesive, i.e. is able after curing of binding strongly to a surface or binding one surface to another.

Besides adhesion and sealing of wet biological tissue, the composition can adhere to and seal a variety of hydrophilic or hydrophobic substrates, natural or synthetic, including polyethylene terephthalate, expanded polyethylene terephthalate, polyester, polypropylene, silicones, polyurethanes, acrylics, fixed tissue (e.g. pericardium), ceramics or any combinations thereof.

Method of Manufacture

The method for manufacturing the composition of the present invention comprises:
i) polycondensation of a first component comprising two or more functionalities of the general formula —OR, where R of each group is independently hydrogen or alkyl; and a second component comprising two or more acid ester functionalities;
ii) activation of the pre-polymer made by step i);
iii) control of anhydride content; optionally
iv) blocking free hydroxyl groups; and/or optionally
v) purification of the activated pre-polymer made by steps ii) and/or iii) and/or iv).

The said first component may be a polyol, such as a diol, triol, tetraol or greater. Suitable polyols include diols, such as alkane diols; triols, such as glycerol, trimethylolpropane, triethanolamine; tetraols, such as erythritol, pentaerythritol; and higher polyols, such as sorbitol. Unsaturated diols, such as tetradeca-2,12-diene-1,14-diol, or other diols including macromonomer diols such as polyethylene oxide, and N-methyldiethanoamine (MDEA) can also be used. Preferably, the polyol is substituted or unsubstituted glycerol.

The said second component may be a polyacid, such as a diacid or higher order acid. A wide variety of diacid, or higher order acids, can be used. Exemplary acids include, but are not limited to, glutaric acid (5 carbons), adipic acid (6 carbons), pimelic acid (7 carbons), sebacic acid (8 carbons), and azelaic acid (nine carbons). Exemplary long chain diacids include diacids having more than 10, more than 15, more than 20, and more than 25 carbon atoms. Non-aliphatic diacids can also be used. For example, versions of the above diacids having one or more double bonds can be used to produce polyol-diacid co-polymers.

Exemplary aromatic diacids include terephthalic acid and carboxyphenoxy-propane. The diacids can also include substituents as well, for example amine and hydroxyl substituents.

Preferably the diacid is substituted or unsubstituted sebacic acid.

The said first and second component are added together in a first component: second component molar ratio range of 0.5:1 to 1.5:1, preferably 0.9:1.1 and most preferred 1:1. Where the first component is glycerol and the second component is sebacic acid and added in a 1:1 molar ratio, there are three hydroxyl groups on glycerol for two carboxyl groups on the sebacic acid. Therefore the extra hydroxyl group on glycerol is used during the activation step.

The conditions for step i) are not especially limited but may include a temperature range of 100 to 140° C., preferably 120 to 130° C., an inert atmosphere, preferably comprising nitrogen, and under vacuum.

The activating agent of step ii) is preferably an acrylating agent which comprises an acrylate group which are moieties containing substituted or unsustituted acryloyl group. The acrylate may contain the following group: —C(=O)—$CR_1$=$CR_2R_3$, wherein $R_1$, $R_2$, $R_3$ are independently from one another, selected in the group consisting of H, alkyl such as methyl or ethyl), aryl such as phenyl, substituted alkyl, substituted aryl, carboxylic acid, ester, amide, amine, urethane, ether, and carbonyl.

Preferably, $R_1$, $R_2$ and $R_3$ are H; or $R_1$ is $CH_3$, $R_2$ and $R_3$ are H; or $R_1$ and $R_2$ are H and $R_3$ is $CH_3$; or $R_1$ and $R_2$ are H and $R_3$ is phenyl.

Most preferably, the acrylating agent is acryloyl chloride.

During the acrylation process, anhydrides can be formed resulting from the reaction of the acrylated monomer with any carboxylic acid groups. According to preferred embodiment, the anhydride content is controlled in step (iii) by ethanol capping or using any other nucleophilic substitution reaction. Suitable reagents for this step (iii) include alcohols, amines or sulfhydryl compounds. The addition of ethanol is preferably at a temperature in the range of 30 to 50° C., preferably 35 to 45° C., for example 40° C. The duration of the ethanol capping step is conducted preferably during 10 and 40 hours, more preferably during 24 hours. The volumetric ratio of polymer solution to ethanol is in the range of 20:1, more preferably in the range of 10:1 and even more preferably in the rage of 5:1.

Hydroxyl blockage or protection may be performed (step iv)). Techniques known in the art can be applied. Preferably, the hydroxyls are blocked through acylation reaction using a compound such as ethanoyl chloride.

Residual levels of grafted anhydrides may also be present, preferably at a level below 0.05 mol/mol of polyacid.

The formation of grafted anhydrides may also be prevented through blockage of any free carboxylic acid groups prior to activation i.e. step (iv) taking place prior to step (ii).

Steps i) to iv) can be carried out in the presence of one or more solvents or catalysts, examples including dichloromethane (DCM), ethyl acetate (EtOAc) dimethylaminopyridine (DMAP), and triethylamine (TEA) or any combination thereof.

The purification step v) is carried out to ensure that any solvents and un-reacted products are removed from the pre-polymer made by step iii) and iv). This step can comprise filtration and/or water washing step. When this step v) comprises water washing step, conditions to allow a fast phase separation between organic and aqueous phase should be favored. For example, phase separation during water washings can be improved by the use of salts solubilized in the aqueous phase. Examples of salts include but are not limited to, sodium chloride, sodium bicarbonate. In alternative, the salts produced during the reaction can be removed through filtration using an organic solvent such as ethyl acetate, n-methyl tetrahydrofurane, tetrahydrofurane.

The purification step may also preferably be followed by one or more, more preferably all of the following steps including addition of free radical inhibitor, for example butylated hydroxytoluene (BHT), monomethylether-hydroquinone (MEHQ), phenylbutyl-nitrone (PBN), and/or photoinitiator, for example Irgacure 2595 or diphenyl-trimethylphosphine oxide (TPO), solvent evaporation and/or extraction, preferably through supercritical $CO_2$ to assure efficient solvent and impurities removal without interfering with the activation of the pre-polymer.

Methods of Using

The composition can be applied directly to the desired site, such as by application with syringe or a catheter, through a spreading tip, by spraying or using a brush. The composition preferably is sufficiently non-viscous as to be injectable through a syringe needle having a gauge of 14 to 20, preferably 14 to 18 but sufficiently viscous to remain in place at the site of administration with minimum washout. The composition can be mixed before application or during application with a photoinitiator, stabilizer, therapeutic, prophylactic, and/or diagnostic agent, and/or one or more excipients.

The materials can be used directly, i.e., applied directly to the site to be sealed or adhered. Alternatively, the materials can be applied to a device, such as a patch or tape, to adhere the patch to the desired site. Conventional patch, patch materials or graft materials, natural or synthetic, known in the art can be used. Patches for use with major blood vessels, cardiac tissue, and/or hard to treat wounds (e.g., diabetic ulcers) are known in the art. Biocompatible, biodegradable surgical tape can be used, for example, to stop bleeding during surgery. Since the tape is biodegradable, it does not need to be removed before the surgeon sutures the wound closed. Examples of other suitable materials include polyethylene terephthalate, expanded polyethylene terephthalate, polyester, polypropylene, silicones, polyurethanes, acrylics, fixed tissue (e.g. pericardium), ceramics or any combinations thereof.

The thickness of the composition or adhesive layer can be varied depending on the application and site of administration. The thickness of the coatings can be at least about 50 microns, 60 microns, 70, microns, 74 microns, 75 microns, 80 microns, 100 microns, 125 microns, 150 microns, 175 microns, 200 microns, 225 microns, 250 microns, 275 microns, 300 microns, 325 microns, 350 microns, 375 microns, 400 microns, 425 microns, 450 microns, 475 microns, 500 microns, 525 microns, 550 microns, 575 microns, 600 microns, 625 microns, 650 microns, 675 microns, 700 microns, or 725 microns.

The sealing and adhesive properties of the activated pre-polymer can be induced through different approaches. The preferred approach is through a light stimulus in the presence of a photoinitiator. Other potential stimuli include heat in the presence of suitable initiators known in the art, or the use of reactive chemicals that can induce the network polymerization as disclosed above.

The sealant/adhesive strength may be improved by subjecting the composition to preload during curing. This may be particularly useful for those embodiments involving a patch where the prepolymer is coated on a patch and then applied to a tissue. The preload applied in the coated patch during curing can vary provided it results in an improvement in adhesive strength. The preload force applied to the patch may be from about 0.5 N to about 10 N, preferably from about 1 N to about 8 N, more preferably from about 2 N to about 8 N, most preferably from about 3 N to about 7 N. The application of preload may help the adhesive penetrate into the tissue.

Uses

A. Tissue Sealing and Adhesion

The composition according to the invention may be used for adhering or sealing targeted surfaces including tissue, graft material such as PTFE-based graft, or any combination thereof. The method for adhering or sealing targeted surfaces comprises applying the composition to the surface and curing the composition.

According to special embodiment, the composition of the Invention is used for forming a barrier or for filling a void, especially in order to prevent leaking, e.g. of fluid, gas, etc. For example, the composition of the Invention can be used as surgical sealant. Examples of applications include stopping bleeding, for example, due to a wound or trauma or during surgery such as after suturing a graft to a vessel or after vascular access in endovascular procedures. Examples of applications include use as adjunct to sutures in vascular anastomosis, and as adjunct to sutures in ePTFE grafts, e.g. ePTFE vascular grafts. The sealant does not need to be removed before or after the surgeon sutures the wound closed since it will degrade over time. According to other applications, the composition of the Invention can further be used in conditions with no suture, e.g. for sutureless closure of vascular incisions. Other types of wounds that can be treated include, but are not limited to, wounds that leak, wounds that are hard to close or that fail to heal properly through normal physiologic mechanisms. The application can be performed both inside and outside the body, for human or veterinary use.

Unlike conventional tissue adhesives that spontaneously activate during application or in the presence of water, or adhesives that are hydrophilic and thus are subject to washout prior to curing, the composition according to the invention can be applied to wet substrates without activation or displacement. The composition can also be applied to dry substrates.

The composition may also be used for adhering tissue to the surface of a medical device. The composition can be used in medical devices, either as part or all of a device or to adhere a device to tissue. The method for adhering tissue to the surface of a medical device comprises applying the composition to the surface of the tissue and/or medical device and curing the composition. The composition can also be used to join tissue, including one or more tissue in vivo.

The composition according to the invention can also be fabricated into a biodegradable stent. The stent can increase the diameter of a blood vessel to increase flow through the vessel, but since the stent is biodegradable, the blood vessel can increase in diameter with a reduced risk of thrombosis or covering the stent with scar tissue, which can re-narrow the blood vessel. The composition can cover an outer surface of a stent to help adhere the stent to a vessel wall in a manner that is less damaging to the tissue than an uncovered stent or avoid its displacement inside the body. Similarly, the composition can cover the surface of any devices which are in contact with tissue to provide a suitable interface that can be adhesive to tissue.

The composition according to the present invention can be used in a variety of other applications where an adhesive or sealant is required. These include, but are not limited to, air leaks following a lung resection; to reduce the time for surgical procedures; to seal dura; to ease laparoscopic procedures; as a degradable skin adhesive; as a hernia matrix to prevent or to reduce the need for stables or tacks; to prevent blood loss; to manipulate organs or tissues during surgical procedures; to secure corneal transplants in place; to patch a heart to deliver drugs and/or to reduce dilation of the heart after myocardial infarction; to attach another material to a tissue; to augment sutures or staples; to distribute forces across tissue; to prevent leaks; as a barrier membrane on the skin to prevent evaporation of water from burnt skin; as a patch for delivery of anti-scar or antimicrobial medication; to attached devices to tissue; to attach devices to mucus membrane as a tape to secure devices within an oral cavity, such as to hold dentures and oral appliances; as a tape to anchor soft tissue to bone; as mouldable barrier in guided bone repair and, preventing the formation of holes in tissue, enhancing/augmenting mechanical properties of tissues, etc.

B. Delivery of Bioactive Molecules

The composition according to the invention described may also contain one or more pharmaceutical, therapeutic, prophylactic, and/or diagnostic agents that are released during the time period that the material functions as a sealant/adhesive. The agent may be a small molecule agent, for example having molecular weight less than 2000, 1500, 1000, 750, or 500 Da, a biomolecule, for example peptide, protein, enzyme, nucleic acid, polysaccharide, growth factors, cell adhesion sequences such as RGD sequences or integrins, extracellular matrix components, or combinations thereof. Exemplary classes of small molecule agents include, but are not limited to, anti-inflammatories, analgesics, antimicrobial agents, and combinations thereof. Exemplary growth factors include, without limitation, TGF-β, acidic fibroblast growth factor, basic fibroblast growth factor, epidermal growth factor, IGF-I and II, vascular endothelial-derived growth factor, bone morphogenetic proteins, platelet-derived growth factor, heparin-binding growth factor, hematopoetic growth factor, peptide growth factor, or nucleic acids. Exemplary extracellular matrix components include, but are not limited to, collagen, fibronectin, laminin, elastin and combinations thereof. Proteoglycans and glycosaminoglycans can also be covalently or non-covalently associate with the composition of the present invention.

Functional groups on the pre-polymer that were not activated may be used to covalently attach one or more agents, such as small molecule agents and/or biomolecules. Alternatively, the one or more agents can be physically entrapped within the cured composition by curing the composition in the presence of the agent.

According to preferred embodiments, slower release profiles of bioactive molecules will be obtained by increasing the degree of acrylation according to the Invention.

C. Tissue Support

The materials can be used to create tissue supports by forming shaped articles within the body to serve a mechanical function. The shaped articles may be produced by a variety of fabrication techniques know in the art, including 3D printing.

Such articles may exert functions such as holding two tissues together or positioning the tissue in a specific position inside or outside the body.

The tissue can be coated with a layer of the materials, for example the lumen of a tissue such as a blood vessel to prevent restenosis, re-closure or vasospasm after vascular intervention.

The composition may also contain one or more types of cells, such as connective tissue cells, organ cells, muscle cells, nerve cells, and combinations thereof. Optionally, the material is seeded with one or more of tenocytes, fibroblasts, ligament cells, endothelial cells, lung cells, epithelial cells, smooth muscle cells, cardiac muscle cells, skeletal muscle cells, islet cells, nerve cells, hepatocytes, kidney cells, bladder cells, urothelial cells, chondrocytes, and bone-forming cells. The combination of cells with the material may be used to support tissue repair and regeneration.

D. Anti-Adhesion Barriers

The materials herein described can be applied to reduce or prevent the formation of adhesions after surgical procedures, for example to prevent adhesion of brain tissue to the skull after brain surgery or implantation of devices to prevent peritoneal adhesion.

E. Other Applications

The compositions can also be used to coat tools, such as surgical instruments, for example forceps or retractors, to enhance the ability of the tools to manipulate objects. The materials can also be used herein can also be used in industrial applications where it is useful to have a degradable adhesive that is biocompatible, for example to reduce potential toxicity of the degradation products, such as marine applications, for example in underwater use or attaching to the surface of boats. The materials can be also used to produce shaped objects by a variety of techniques known in the art, including 3D printing. The shaped object may have micro or nanoscale resolution.

The present invention will now be illustrated, but in no way limited, by reference to the following examples.

EXAMPLES

The following general protocol was initially applied to synthesize poly glycerol sebacate (PGS) pre-polymer:
1. Equimolar amounts of glycerol and sebacic acid were weighed.
2. The reaction mixture temperature set between 120 and 130° C. until the monomers were completely melted.
3. Upon melting of the reagents the bath or reaction temperature was reduced to the target value of 120° C. and stirring started.
4. The air inside the flask was replaced with nitrogen using three vacuum/purging cycles.
5. The reaction was followed for 8 hours.
6. The nitrogen supply was then removed and the pressure reduced using a vacuum pump set to a target of 15mBars.

The reaction was followed until the targeted Mw (about 3000 Da) and polydispersity (<3) were achieved. The glycerol: sebacid acid molar ratio targeted was 1:1. The PGS pre-polymer obtained was activated through the reaction of PGS with acryloyl chloride in the presence of TEA, followed by purification through filtration or water washing.

The PGS polymers obtained could be acrylated but a high variability in molecular weight evolution during PGSA synthesis and storage was observed. The root cause for instability can be attributed to anhydride instability.

One month term stability studies of 50% w/w solutions of the activated pre-polymer in DCM revealed continued molecular weight progression even at −18° C. storage conditions. A band in FTIR at 1810 cm$^{-1}$ and triplets in NMR at 2.4 and 2.5 ppm were detected and attributed to anhydride by-products formed by the reaction of acryloyl chloride and free carboxylic acids. The intensity of the triplets decreased over time during storage and therefore could be linked to the PGSA 50% w/w Mw evolution.
1. PGS pre-polymer was synthesized as described above.
2. Overnight acrylation of PGS pre-polymer with AcCl (0.8 mL per 5 grams of polymer) in 10% w/v DCM in the presence of DMAP (1mg per gram of polymer), TEA (1.4 mL per 5 grams of polymer) and 200 ppm BHT. The quantities of AcCl and TEA can be adjusted to achieve different degrees of acylation.
3. Ethanol capping at 40° C. during synthesis, to eliminate anhydrides and prevent Mw growth during synthesis and storage. A volume ratio of ethanol to DCM of 1:5 was used.
4. Partial evaporation of ethanol and DCM
5. Purification through water washing
6. Addition of 400 ppm BHT
7. Partial solvent evaporation to reach 50% w/w solution in DCM followed by the addition of 200 ppm of MEHQ and storage at 4° C.
8. Incorporation of Irgacure 2959 (2-Hydroxy-4'-(2-hydroxyethoxy)-2-methylpropiophenone or Irgacure 651 (2,2-Dimethoxy-1,2-diphenylethan-1-one) or Irgacure TPO (diphenyl(2,4,6-trimethylbenzoyl)phosphine oxide) and solvent removal through supercritical $CO_2$ Where anhydrides were eliminated during synthesis, as confirmed by the decrease of the bands associated with anhydrides in FTIR and NMR, it was observed that ethanol capping led to a decrease of the degree of acylation of PGSA, likely due to cleavage of the acrylate anhydride that leads to the release of acrylic acid and ethyl acrylate removed during the purification/supercritical $CO_2$ steps.

Regarding stability, limited evolution in Mw was observed for the product stored in 50% w/w solution at −20° C. For the dry product limited Mw changes were observed after 12 months when stored at −20° C. and the product appeared stable. Mw was determined through Gel Permeation Chromatography using equipment with the following specifications:

The GPC equipment used had the following specifications:

Column—LT6000L, (300×8) mm, 10 μm equipped with a precolumn CLM3008 (10×4.6) mm

Flow rate—1.0 mL/min

Injection volume—100 μL

Column temperature—35° C.

Refractometer temperature—35° C.

Elution mode—Isocratic

Mobile phase—Tetrahydrofuran (THF)

Example 1: Burst Performance Testing—Examples A and B

Several stable polymers, without anhydrides, were then evaluated in a burst model to determine their capacity to seal vascular defects. In all cases PGSA starting from PGS with MW of ~3000 Da manufactured according to the method described above was used.

PGSA burst performance was evaluated for sealing a 6 mm in diameter ePTFE graft sutured to porcine carotid artery. Before glue application, the suture line started leaking at about 10 mmHg. Approximately 0.2 mL of PGSA was applied around the suture line using a syringe and the formulation was cured with light for approximately 1 minute. The burst performance is enhanced and the pressure at which the suture line started leaking was measured. Burst values above 150 mmHg could be obtained.

Viscosity of the initial pre-polymer was a key parameter for PGSA burst performance. The viscosity of PGSA was dependent on the degree of acylation and the application temperature as summarized in the table below:

| Example | Degree of Acrylation | Viscosity at room temperature (cP) | Viscosity at 37° C. (cP) |
|---------|---------------------|-----------------------------------|--------------------------|
| A | 0.3 | ~17000 | ~4200 |
| B | 0.5 | ~9800 | ~3500 |

Polymers in examples A and B have equivalent weight average molecular weight.

Viscosity analysis was performed using a Brookfield DV-II+Pro viscosimiter with a 2.2 mL chamber and SC4-14 spindle. The speed during the analysis was varied from 5 to 80 rpm.

Both formulations A and B contained Irgacure 2959 as photoinitiator and were light activated using a Omnicure S100 equiped with a 320-390 nm filter, 70% intensity with borosilicate at the tip.

The formulations with the above acrylation degrees were tested at different temperatures and demonstrated better burst performance than Fibrin in sealing 2 mm longitudinal incisions against porcine carotid arteries. The results are shown in FIG. 1.

Example A had poor spreadability at room temperature which was improved by heating the product to 37° C. (decreasing viscosity) along with enhanced burst performance. Example B had good spreadability at room temperature (lower viscosity with higher degree of acrylation) with enhanced burst performance. Overall, for both examples significantly improved burst performance was achieved compared to commercially used Fibrin.

Figure 2:
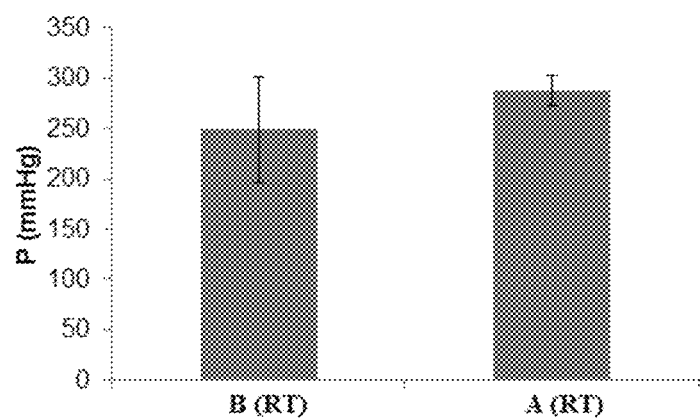

PGSA also presented better burst performance against ePTFE substrates than vascular tissue. The burst pressures of Examples A and B in sealing a 2 mm longitudinal incision in ePTFE are shown in FIG. 2. The maximum force that could be achieved in this set up was ~300 mmHg since intact ePTFE starts leaking at this pressure.

Figure 3:
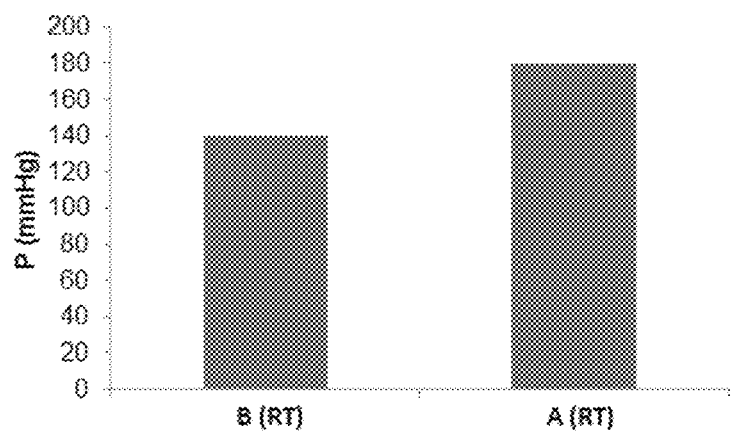

PGSA also demonstrated good burst performance in ePTFE vascular grafts as adjunct to sutures. PGSA burst performance was evaluated to seal a 5 mm in diameter ePTFE graft sutured to porcine carotid artery. Before glue application, the suture line starts leaking at about 10 mmHg. Upon PGSA application, the burst performance is enhanced and the suture line starts leaking at the pressures shown in FIG. 3.

Figure 4:
FIG. 4 is a photograph of a femoral artery graft sealed using a composition according to the present invention.

The efficacy was validated in vivo in a sheep animal model of femoral artery graft with successful results as shown in FIG. 4.

Overall, as well as excellent stability PGSA without anhydrides presented sufficient performance to be used as adjunct to sutures in ePTFE vascular grafts.

Example 2: Burst Performance of PGSA Formulation According to the Invention With Different Photoinitiator Systems Burst testing was conducted to evaluate the sealing capacity of the different formulations comprising different photoinitiator systems (example B, C and D) on ePTFE-vessel anastomosis created by suturing. A lower number of sutures (8-10 running sutures) corresponding to conditions that would normally be employed by a surgeon were used to assure suture line leak. Formulations B, C and D have equivalent weight average molecular weight and degrees of acrylation (i.e. 0.5).

The sealant for testing was applied along the suture line and cured with light, as specified in the table below.

| Example | Photoinitiator | Light activation conditions |
|---------|---------------|----------------------------|
| B | Irgacure 2959, ~0.1% w/w, Incorporated during scCO2 extraction step | Omnicure S1000 equiped with a 320-390 nm filter, 70% intensity with borosilicate at the tip, 60 seconds |
| C | Irgacure 651 (1% w/w) Incorporated through manual mixing | Opsytec 365 nm LED, 10% intensity, 120 seconds |
| D | CQ (1% w/w) and EDB (1% w/w) incorporated through manual mixing | Smarlite Focus blue LED, 460-490 nm, ~300 mW/cm$^2$, 60 seconds |
| E | Irgacure TPO (0.5% w/w) incorporated through manual mixing | ThorLabs LED, 405 nm, 600 mW, 3 × 30 seconds |

CQ/EDB = camphorquinone/Ethyl-4-dimethylamino benzoate

Figure 5:
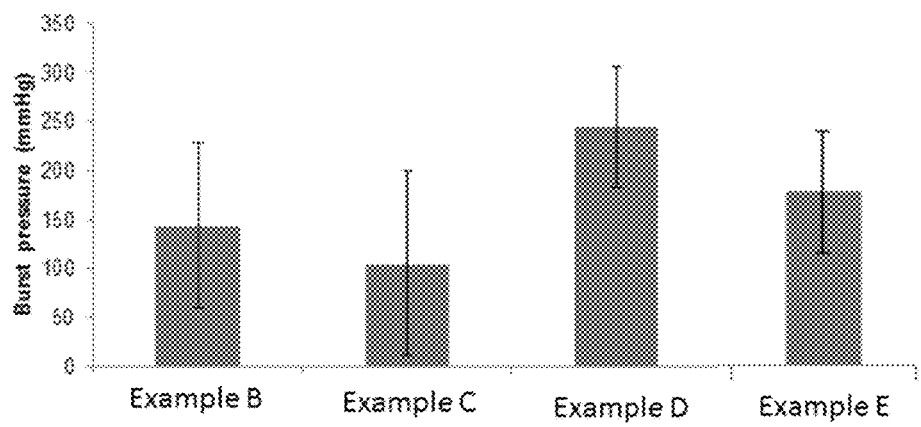

Water was pumped into the vessel at a rate of 80 mL/min. Burst strength for the different formulations was recorded as the maximum pressure achieved during testing. The results are reported in FIG. 5. Overall, equivalent burst performances were found independently of the photoinitiator/light source system used. Of note, the formulation with CQ/EDB demonstrated strong sensitivity to ambient light, while the other formulations could be easily handled under ambient light without visible gelification/crosslinking for at least 15 minutes.

Example 3: Biocompatibility

PGSA with a degree of acrylation of ~0.45 mol/mol of glycerol and a weight average molecular weight of ~5.000 Da, was evaluated for biocompatibility, according to ISO 10993 (including cytotoxicity, Inflammatory response, Genotoxicity, hemocompatibility, biodegradation). At clinical dosage no biocompatibility issue has been identified.

Example 4: Performance and Biocompatibility in Bone

A wide range of barrier materials have been used in guided bone regeneration. Despite being used in clinical practice, these materials still suffer from limitations namely the need of surgical excision (non-resorbable materials), premature resorption and batch to batch variability (resorbable materials of natural origin).

PGSA has interesting properties to be applied as a moldable barrier in guided bone repair, which include its viscosity prior polymerization (easily mouldable), hydrophobicity (not easily washed away in wet environments), and rapid on-demand polymerization (promoting fixation to the substrate). These properties make it ideal for sealing wet tissues, even in difficult to access anatomical sites.

Figure 6:
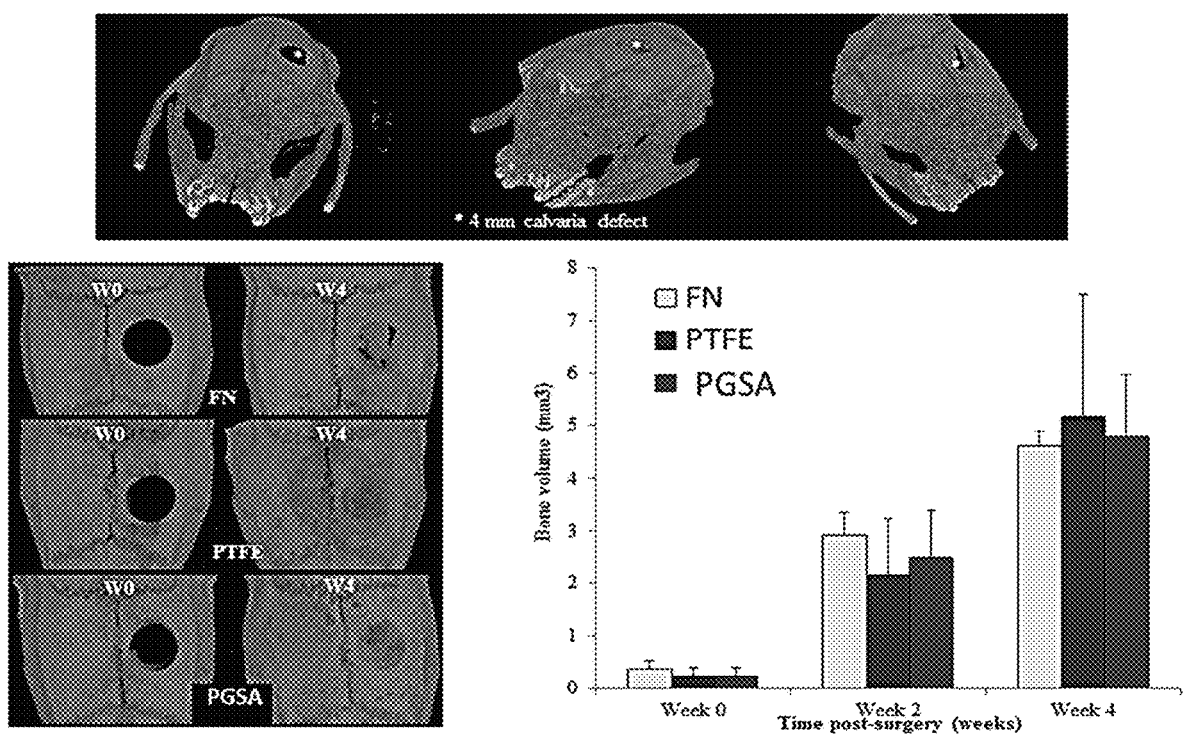
FIG. 6 represents bone growth in a calvarian bone defect in the presence of fibrin alone (FN), fibrin coated with polytetrafluoroethylene (PTFE), or fibrin coated with polyglycerol sebacate acrylate (PGSA). It shows a 3D representation of a rat head, 3D tomo-densitometric reconstruction of calvaria defects at week 0 and week 4, and volume of new bone formation in calvaria defects with different membranes.

PGSA adhesion to bone was evaluated through mechanical testing and has revealed interesting adhesion. To investigate biocompatibility aspects, PGSA membranes of the Invention were implanted as a barrier between periosteum and non-critical sized rat bone defects filled with a fibrin hydrogel (to prevent membrane invagination within the defect). The bone ingrowth in these defects was then compared by micro-computed tomography to one of the defects filled with fibrin glue alone or fibrin glue plus PTFE membranes. No post-surgical complications, infection, changes in body weight, animal behaviour, or general health problems were observed for the 4 weeks of implantation. In all groups, healing of the tissue was uneventful. At 4 weeks, new bone formation was similar in all groups (PGSA 4.7±1.18 mm$^3$, Fibrin alone 4.6±0.27 mm$^3$ and PTFE:

5.1±2.32 mm³) establishing the good biocompatibility of the PGSA membranes and supporting use of the material of the Invention in bone repair applications. These results are reported in FIG. 6 (top image is 3D representation of the calvaria defect at week 0; bottom left image is a 3D tomo-densitometric reconstruction of calvaria defects at week 0 and best week 4; bottom right image is a graph representing the volume of new bone formation in calvaria defects filled with either fibrin alone, fibrin and ePTFE membrane or fibrin and PGSA membrane).

Example 5: Incorporation of Coloring Agent

It can be desirable for some applications to have coloured material. The feasibility of incorporating a coloring agent during the manufacturing of the sealant PGSA of the Invention was evaluated.

FD&C 1 was used as testing agent. The FD&C 1 containing PGSA was prepared according to the following steps:
1. FD&C 1 solution was prepared by mixing 0.2 g of FD&C 1 in 25 ml of Ethanol.
2. The solution was stirred and filtered (0.2 μm pores).
3. 3 μl of this solution (24 pg of Erioglaucine) were added per gram of PGSA solution (50% w/w in dichlorometha)
4. The solution was purified and solvents removed using supercritical carbon dioxide processing.

Upon supercritical $CO_2$ extraction, the final concentration of FD&C 1 in the final product is ~50 ppm. This quantity allowed reaching a blue colour sealant that keeps its transparent properties, while allowing better visualization once applied to the targeted substrate. It has thus been shown that incorporation of coloring agent does not affect the polymerization kinetics or the sealing properties of PGSA.

Example 6: Polymerization Using Redox Agent

The feasibility of polymerizing PGSA of the Invention in the presence of redox agents was evaluated. Briefly, the following methodology was followed:
1. The targeted quantities of Reducer and Oxidizer were obtained and grinded if possible (or solubilized if necessary).
2. 0.5 g of PGSA was warmed at 37° C. for 15 minutes.
3. PGSA was mixed with the targeted quantity of Oxidizer, and after, mixed with the Reducer.
4. Polymerization was evaluated macroscopically The results obtained are summarized in the table below.

| Reducer | Oxidizer | Polymerization |
|---|---|---|
| 4 N,N Trimethyl-aniline →1.88% w/w | Ammonium Persulfate →1.164% w/w | Yes |
| 4 N,N Trimethyl-aniline →0.94% w/w | Benzoyl Peroxide →0.11% w/w | Yes |
| 4 N,N Trimethyl-aniline →0.82% w/w | TertButylperoxy-benzoate →0.71% w/w | Yes |
| TEMED →3.1% w/w | Ammonium Persulfate →1.164% w/w | No |
| TEMED →3.1% w/w | Benzoyl Peroxide →0.22% w/w | No |
| TEMED →0.62% w/w | TertButylperoxy-benzoate →0.54% w/w | No |
| Ac. Ascorbic →16% w/w | Ammonium Persulfate →5.82% w/w | Yes |
| Ac. Ascorbic →16% w/w | Benzoyl Peroxide →0.66% w/w | No |
| Sodium bisulfite (NaHSO3) →4.2% w/w | Ammonium Persulfate →5.82% w/w | No |
| 3-(Dimethylamino) propionitrile. →4.35% w/w | Ammonium Persulfate →2.91% w/w | No |
| Mohr's salt →2.69% w/w | Ammonium Persulfate →2.91% w/w | No |

Concentrations reported in the table are in relation to PGSA dry weight.

Example 7: Use in Drug Delivery

The feasibility of releasing small molecules from photo-cured (405 nm LED, ~100 mW/cm²) cured PGSA was evaluated. The model molecule hydrochlorotiazide was used for this study.

7.1. First, different techniques were used to incorporate the drug in the polymer:
1. Incorporation through manual mix of the drug crystals with PGSA pre-heated at 37° C.
2. Incorporation through the use of solvents, followed by solvent evaporation Polymerized PGSA disks of defined drug loading and size were prepared. The release profile of the drug was evaluated after immersion of the disks in PBS at 37° C. and under shaking. The supernatant was removed at specified time points and the concentration of released drug measured using UV/Vis spectroscopy.

The techniques used to incorporate the drug in the polymer did not seem to have a major impact on the release profiled observed.

Figure 7:
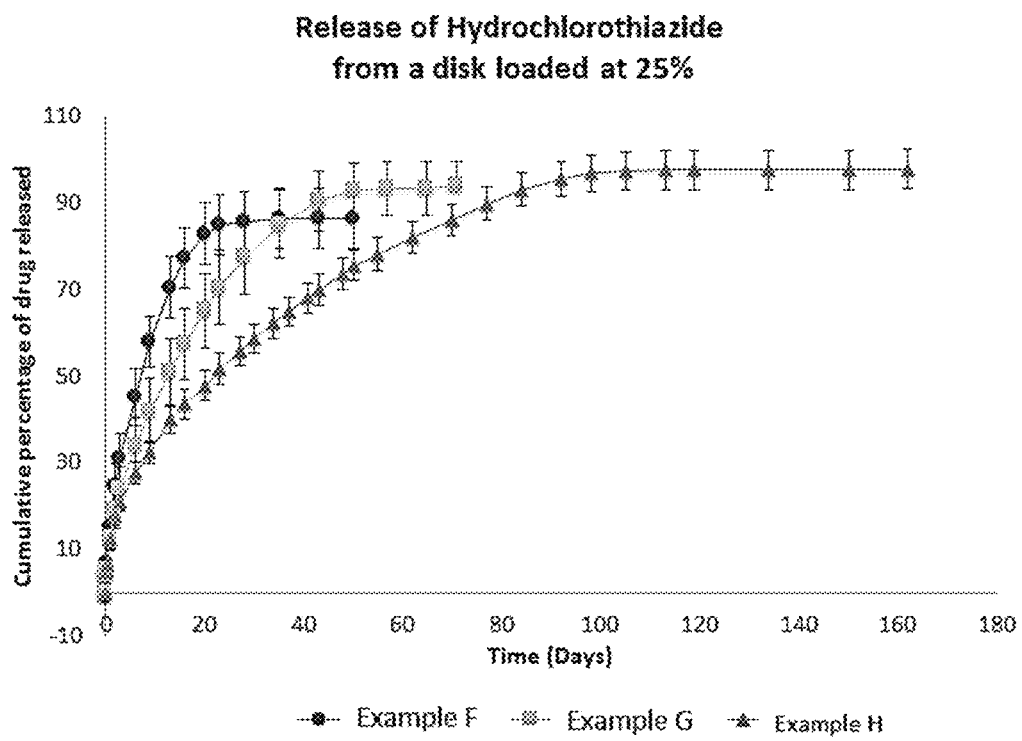
FIG. 7 is a graph showing the release of a model drug from PGSA disks with different thicknesses.
Figure 8:
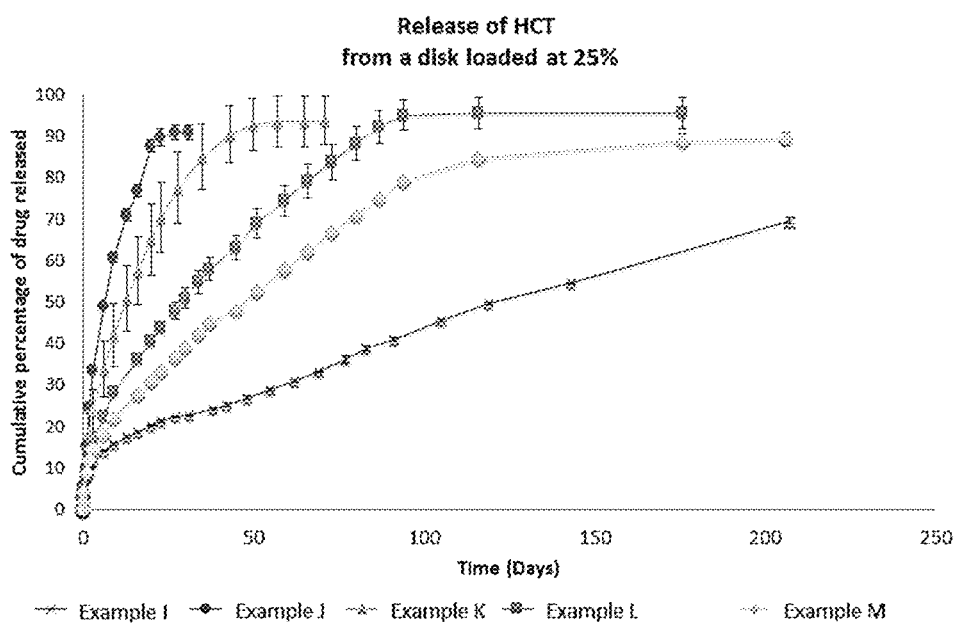
FIG. 8 is a graph showing the release of a model drug from PGSA disks with different degrees of acrylation.

7.2. Different strategies were then tested to tune the release profile of the encapsulated drug
1. Change in Polymer Disk Geometry:
   For a 6 mm diameter disk of PGSA of the Invention, the release profile could be tuned by changing the thickness of the disk, as reported in FIG. 7. Example F represents a disk 200 μm thick (n=4), Example G represents a disk 400 μm thick (n=4), Example H represents a disk 800 μm thick (n=6). Thicker disks lead to a slower release profile.
2. Change in Polymer Degree of Acrylation:
   The use of PGSA of the Invention with different specifications allows tuning the drug release profile. This was demonstrated by preparing a range of PGSA derivatives with different degrees of acrylation that were used to encapsulate hydrochlorothiazide under equivalent conditions. Increasing the degree of acrylation results in slower release profiles. The results are reported in FIG. 8. The degree of acylation (mol/mol of glycerol) is shown in the table below:

| Example | Degree of acrylation (mol/mol of glycerol) |
|---|---|
| I | 0.95 |
| J | 0.32 |
| K | 0.45 |
| L | 0.95 + 0.32 on 1:1 mass ratio |
| M | 0.95 + 0.45 on 1:1 mass ratio |

Example 8: 3D Printing

PGSA of the invention was 3D printed using a commercially available Autodesk Ember 3D printer, equipped with a 405 nm LED using the Direct Light Processing (DLP) method. The 3D printer was custom modified to enable the use of small PGSA volumes, and the viscous liquid PGSA pre-heated to ~100° C. to decrease its viscosity. Furthermore, PGSA was doped with a UV blocker compound (Mayzo OB+) to control light diffusion properties.

Under these conditions, the following printing parameters were evaluated as preferred:

| First layer time (Sec) | Burn in layer time (Sec) | Model layer time (Sec) | Seperation Angle (Deg) | Resin Tray Temperature (Celsius) | LED Power (%) | Z axes seperation lift (mm) | Seperation sweep speed (RPM) |
|---|---|---|---|---|---|---|---|
| 4 | 4 | 2 | 5 | 100 | 58.8 | 750 | 4 |

Figure 9:
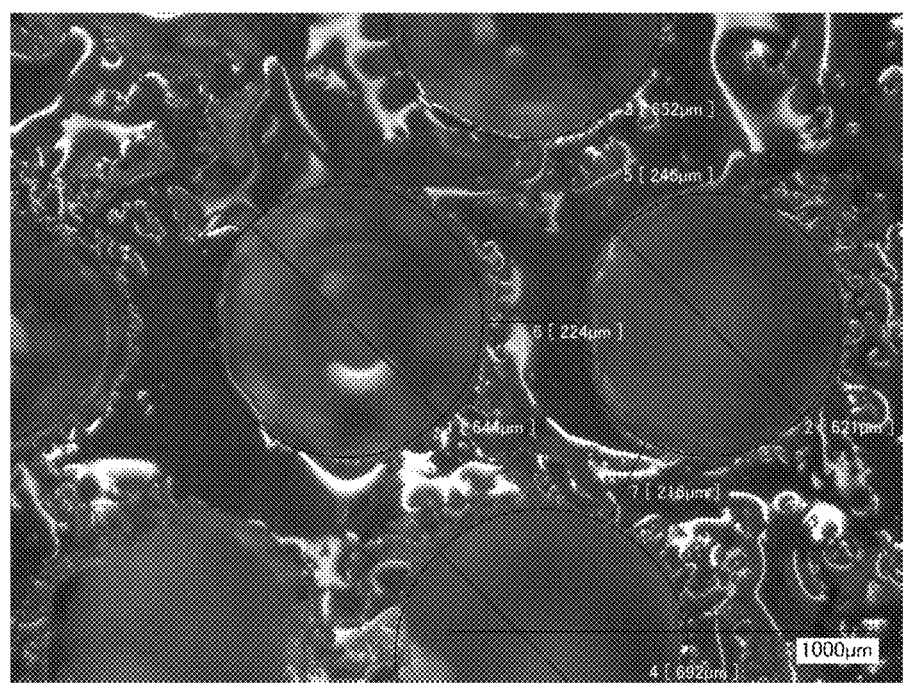
FIG. 9 is a picture of 3D printed PGSA.

Structures with micrometer scale resolution could be printed, as detailed in FIG. 9.

Example 9

Performance of PGSA of the Invention has been compared with a commercially available sealant (glutaraldehyde (B SAG)) in an in vivo porcine model for sutureless closure of vascular incisions.

2 mm defects of the carotid artery (CA) and jugular vein were created and closed with PGSA of the Invention or bovine serum albumin and glutaraldehyde (B SAG) without the use of sutures.

These experiments have shown that PGSA of the Invention effectively seals defects of vessels and showed no signs of stenosis and low inflammatory reaction in contrast to BSAG.

The invention claimed is:

1. A method for producing a shaped article comprising a step of 3D printing a composition, wherein the composition comprises:
activated pre-polymers having a moiety derived from a polyol and a moiety derived from a polyacid as depicted in formula (I):

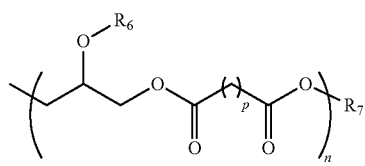

wherein:
each n individually represent an integer equal to or greater than 1 and each p represent an integer from 4-10;
$R_6$ in each individual unit is independent and can be:
(i) a polymer chain;
(ii) —C(=O)—$CR_3$=$CR_4R_5$, where $R_3$, $R_4$, $R_5$ are, independently from one another, selected from H, alkyl, aryl, substituted alkyl, substituted aryl, carboxylic acid, ester, amide, amine, urethane, ether, and carbonyl; or
(iii) —H, alkyl, acyl, aryl, heterocycles, cycloalkyl, aromatic heterocycles, multicycloalkyl, ester, ether, halide, carboxylic acid, amino, alkylamino, dialkylamino, trialkylamino, amido, carbamoyl, thioether, thiol, alkoxy, or ureido groups;
provided that for at least one individual unit in said activated prepolymers, $R_6$ is —C(=O)—$CR_3$=$CR_4R_5$;
$R_7$ is selected from the group consisting of alkyl, aryl, substituted alkyl, substituted aryl, amine, urethane, thiol, or thioester;
wherein at least one of said activated pre-polymers of said composition comprises a terminal carboxyl group that is protected by a group selected from alkyl, aryl, substituted alkyl, substituted aryl, amine, urethane, thiol, or thioester;
wherein when said composition comprises activated pre-polymers with grafted anhydride, said composition has a molar ratio of grafted anhydride to the polyacid of less than 0.05 mol/mol; and
wherein the activated pre-polymers are formed by activating pre-polymers having a weight average molecular weight of from about 3000 to about 5000 Daltons and a polydispersity of less than 3.

2. The method according to claim 1, wherein the composition comprises no anhydride.

3. The method according to claim 1, wherein p=8.

4. The method according to claim 1, wherein the activated pre-polymers are polyglycerol sebacate acrylate.

5. The method according to claim 1, wherein the activated pre-polymers have a degree of activation between 0.25 and 0.8 mol/mol of polyacid.

6. The method according to claim 1, wherein the activated pre-polymers have a degree of activation of 0.5 mol/mol of polyacid.

7. The method according to claim 1, wherein the composition further comprises a photo-initiator.

8. The method according to claim 7 wherein the composition further comprises a UV blocker compound.

9. A shaped article obtainable by the method according to claim 1.

10. The method according to claim 1, wherein $R_7$ is —$CH_2CH_3$.